United States Patent
Yoo

(10) Patent No.: US 7,095,223 B2
(45) Date of Patent: *Aug. 22, 2006

(54) METHOD OF LOCATING AN ANOMALY IN A TUBULAR MEMBER IN A WELL

(75) Inventor: Kwang M. Yoo, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/882,818

(22) Filed: Jul. 1, 2004

(65) Prior Publication Data

US 2004/0239316 A1  Dec. 2, 2004

Related U.S. Application Data

(63) Continuation of application No. 10/121,399, filed on Apr. 12, 2002, now Pat. No. 6,815,946, which is a continuation-in-part of application No. 09/286,362, filed on Apr. 5, 1999, now Pat. No. 6,411,084.

(51) Int. Cl.
*E21B 47/09* (2006.01)
*G01N 27/72* (2006.01)
*G01R 33/12* (2006.01)

(52) U.S. Cl. ............... 324/221; 324/235; 166/255.1

(58) Field of Classification Search .............. 324/221, 324/220, 219, 235, 239, 240; 166/66.5, 255.1
See application file for complete search history.

(56) References Cited

U.S. PATENT DOCUMENTS

| | | | |
|---|---|---|---|
| 3,015,063 A | | 12/1961 | Ownby |
| 3,570,594 A | | 3/1971 | Hamilton |
| 4,013,945 A | * | 3/1977 | Grosso ............... 324/207.25 |
| 4,087,749 A | | 5/1978 | McCormack |
| 4,634,978 A | | 1/1987 | Watanabe |
| 4,794,336 A | * | 12/1988 | Marlow et al. ............. 324/221 |
| 4,852,263 A | | 8/1989 | Kerr |
| 4,918,824 A | | 4/1990 | Farrar |
| 5,251,170 A | | 10/1993 | Daughton et al. |
| 5,329,269 A | | 7/1994 | Watson |
| 5,361,838 A | | 11/1994 | Kilgore |
| 5,420,819 A | | 5/1995 | Pohm |
| 5,424,236 A | | 6/1995 | Daughton et al. |
| 5,526,022 A | | 6/1996 | Donahue et al. |

(Continued)

FOREIGN PATENT DOCUMENTS

EP  0014195  1/1980

(Continued)

OTHER PUBLICATIONS

Nonvolatile Electronics, Inc. brochure, May 1998.

*Primary Examiner*—Jay M. Patidar

(57) ABSTRACT

A detector assembly and methods including a magnetoresistive sensor capable of detecting anomalies in the wall of a casing string disposed in a wellbore. Examples of anomalies include gaps between casings such as due to casing joints, air gaps in casing threads such as due to flush casing joints, enlarged casing wall thickness such as due to external casing collars, damaged casing, perforations, and other discontinuities or deformities in the casing. The detector assembly and methods detect perturbations in the earth's magnetic field caused by the anomalies. The detector assembly generates essentially no magnetic or electromagnetic field so that other downhole instrumentation is not affected by its presence.

3 Claims, 11 Drawing Sheets

U.S. PATENT DOCUMENTS

| | | |
|---|---|---|
| 5,532,587 A | 7/1996 | Downs et al. |
| 5,569,544 A | 10/1996 | Daughton |
| 5,595,830 A | 1/1997 | Daughton |
| 5,617,071 A | 4/1997 | Daughton |
| 5,636,159 A | 6/1997 | Pohm |
| 5,720,345 A | 2/1998 | Price et al. |
| 5,729,137 A | 3/1998 | Daughton et al. |
| 5,768,180 A | 6/1998 | Pohm |
| 5,831,426 A | 11/1998 | Black, Jr. et al. |

FOREIGN PATENT DOCUMENTS

| | | |
|---|---|---|
| GB | 2109113 A | 5/1983 |
| GB | 2143331 A | 2/1985 |
| GB | 2327501 | 1/1999 |
| WO | WO 98/12554 | 3/1998 |

* cited by examiner

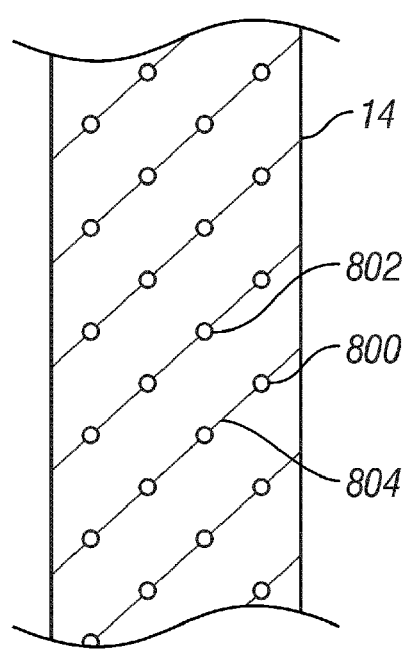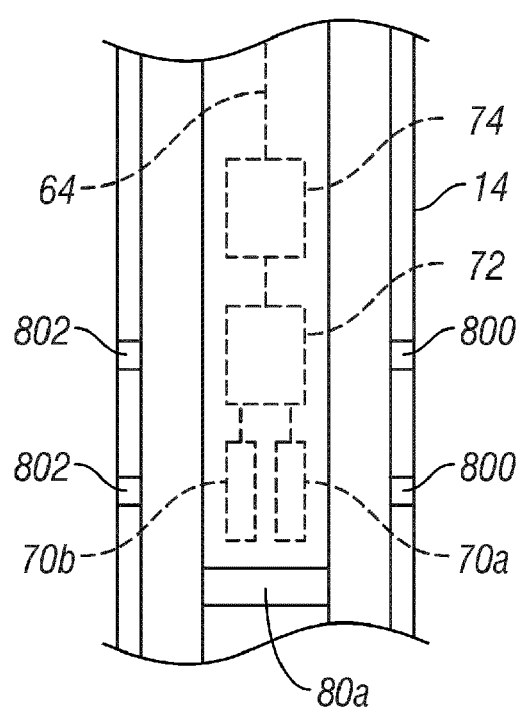
FIG. 11                    FIG. 12

METHOD OF LOCATING AN ANOMALY IN A TUBULAR MEMBER IN A WELL

CROSS-REFERENCE TO RELATED APPLICATIONS

The present application is a continuation of U.S. patent application Ser. No. 10/121,399, filed Apr. 12, 2002 now U.S. Pat. No. 6,815,946 and entitled Magnetically Activated Well Tool, hereby incorporated herein by reference for all purposes, which is a continuation-in-part of U.S. patent application Ser. No. 09/286,362, filed Apr. 5, 1999 now U.S. Pat. No. 6,411,084 and entitled Magnetically Activated Well Tool, hereby incorporated herein by reference for all purposes.

STATEMENT REGARDING FEDERALLY SPONSORED RESEARCH OR DEVELOPMENT

Not Applicable.

BACKGROUND OF THE INVENTION

1. Field of the Invention

The present invention relates to locators for locating anomalies in a casing string for a wellbore such as casing joints. More particularly, the invention relates to apparatus and methods for detecting, identifying, and locating anomalies in strings of tubular members by sensing the natural magnetic fields induced within the string, such as perturbations in the natural magnetic fields due to fringe effects caused by the anomalies.

2. Description of the Related Art

Casing collar locators are used to locate joints within the borehole casing. The locator is suspended on a wireline cable and passed through the cased borehole. The locator detects the collars used at joints in the casing string as the locator is moved upwardly and/or downwardly through the casing. Various types of casing joints are used to connect adjacent ends of the casing section in a threaded engagement, such as upset joints and exterior collar joints. As the locator moves adjacent to a casing joint, it detects a change in the magnetic readings resulting from the change in casing thickness, or change in mass of metal associated with the casing wall or it detects a change in the polarity of adjacent sections of casing.

Casing collar locators are extremely important tools for downhole operations. They are required for depth correction operations and for the accurate placement of downhole tools, such as anchors, bridges, whipstocks, profiles, and packers. For example, it is desired to avoid setting a downhole tool on a casing joint since the joint presents a gap or discontinuity in the casing wall that may prevent the downhole tool from sealing or anchoring properly.

In order to detect a casing joint, conventional casing collar locators typically rely on the generation of a relatively powerful magnetic field from the locator using either a permanent magnet or by passing a current through a coil to induce magnetism. A significant amount of power is required to generate the magnetic field. As the coil passes adjacent a casing joint, the flux density of the magnetic field is changed by the variation in the thickness of metal provided by the joint. The change causes an electrical output signal to be generated that indicates the presence of the casing joint, and this output signal is transmitted to the surface of the well through a wireline.

Unfortunately, conventional casing collar locators suffer from operational disadvantages and limitations of their effectiveness. Conventional locators are not greatly sensitive, in general, to discontinuities, anomalies, or other changes in the wall of the casing because prior art locators are necessarily large and often several inches to a few feet in length. This causes the locators to have a large resolution such that they cannot detect changes in the magnetic fields of the casing that are less in length than the locator. Thus, such prior art locators are insensitive to small anomalies in the casing.

As a result of not having a high resolution, conventional casing collar locators are reliable only in a "dynamic" mode wherein the locator is moved rapidly through the wellbore casing in order to accurately detect the presence of casing joints. If the locator is moved too slowly, the changes in the signal indicative of the presence of a casing joint, such as a collar, may be too gradual to be recognized by the well operator. Dynamic location of casing joints thus is disadvantageous because it tends to provide less accurate real-time information concerning the position of the casing joint. For example, if it is desired to set a packer five feet below a particular casing joint in a wellbore, a conventional casing collar locator would be moved rapidly either upwardly or downwardly through the wellbore until the particular casing joint is detected. When that occurs, a signal is provided to the wellbore operator which indicates the location of the joint. Due to movement of the locator through the casing, however, the casing collar locator is no longer positioned proximate the casing joint by the time the operator receives the signal and reacts to it by stopping movement of the locator. The precise position of the casing joint must then be somewhat approximated given the current position of the locator within the wellbore.

Additionally, conventional locators locate casing joints by detecting a difference in thickness of the casing wall such as the presence of an external upset or collar. These devices are actually, "collar" locators rather than "joint" locators. As a result, they are unable to reliably detect a "flush" joint where the casing wall thickness is not appreciably altered by the presence of the joint. A joint is considered flush where the adjacent casing sections are threaded directly to one another or where the upset or collar is unusually thin or contains very little metal.

In addition, because conventional casing collar locators generate a significant magnetic field, they tend to interfere with other downhole instrumentation that rely upon accurate magnetic readings. For example, a compass-type magnetometer that is attempting to find magnetic north can be confused by the magnetic field generated by the casing collar locator. Some induction-type locators are known that generate and transmit strong electromagnetic waves, rather than magnetic fields, to detect casing joints. Unfortunately, these devices also tend to interfere with downhole instrumentation.

A need exists for a locator that can more reliably detect the presence of casing section joints in a wellbore and particularly flush joints that do not employ radially enlarged upsets or collars. Further, a need exists for a locator that generates a minimal or no magnetic field that affects the operation of other downhole instrumentation.

In addition, a need exists for a detector that can detect, identify, and/or locate anomalies, such as deformities, discontinuities, perforations and the like, in a cased borehole. To locate the depth and angular orientation of a perforation, for example, requires a very sensitive locator because of the small size of the perforation. The perforation generally is less than one inch in diameter and typically only one-fourth inch in diameter, thus providing a very small change in the continuity of the casing wall and requiring a very sensitive locator.

By way of background, to complete a well, the cased borehole is perforated adjacent the formation to be produced. A perforating trip is made by lowering into the well bore a perforation tool mounted on the lower end of a wireline or tubular work string. The perforation tool or "gun" assembly is then detonated to create a series of spaced perforations extending outwardly through the well casing, the cement holding the casing in place in the wellbore, and into the production zone. Although these perforations may have a random pattern, typically the perforations are made in a spiral pattern around the casing string.

Often the well is treated to enhance production. Well treatment may include treating the formation with chemicals, "fracturing" or a "fracing" the formation, injection of high pressure fluids, acidizing, jetting, or pumping proppant into the formation to maintain the fractures in the formation. The well is treated or stimulated by pumping fluids through the perforations and into the formation. For example, during fracing, a tubular discharge member having a series of spaced discharge ports is lowered into the well on a work string. Packers are set above and below the perforations to form an isolated region. The discharge ports are preferably aligned with the perforations. A slurry is then pumped down the workstring and discharged through the ports in the discharge member causing the slurry to flow through the perforations and into the surrounding production zone. The slurry may include proppant or other treatment fluid.

Well treatment techniques have several well known problems, limitations, and disadvantages. For example, when the discharge member is lowered into the well bore, it is difficult to obtain a precise alignment (in both the axial and angular directions) between the discharge ports in the discharge member and the perforations in the casing. The usual result is that some degree of misalignment exists between the discharge ports and the perforations. When the ports and perforations are not in alignment, the high pressure fluid must follow a tortuous path before entering the perforations after it is discharged from the discharge member. Because the treatment fluid is discharged at a very high pressure and often is highly abrasive, this tortuous flow path can cause severe abrasion and wear problems in the casing.

In addition, it is important that the packer or packers not be set in the perforated region of the casing. If a packer is set in the area having the perforations, the fluid flowing out of discharge ports and through the perforations into the formation may flow back into the wellbore annulus through perforations that are above or below that portion of the wellbore annulus that is isolated by the packers. Turbulence caused by the high pressure and abrasive fluid flowing back into the annulus creates a pressure differential across the packers and tends to erode or "wash out" and ruin the packers. Additionally, it is important that the packer or packers not be set within a casing joint, but instead be set in blank pipe. Typically, there are gaps between the aligned ends of casing sections at the casing joints. If the packer is set in this region, then the packer will not seal properly and hold pressure to isolate the intended interval. When this occurs, the treatment fluid can pass out of the interval and into the annulus and wash out and erode the packer. Accordingly, it is critical to know the location of the perforations and the casing joints to ensure that the packer is not set within the perforations or within a casing joint. Unfortunately, properly positioning the packer with respect to the perforations and casing joints has been difficult to achieve.

Furthermore, even if the depth of the discharge member is precisely known, there still exist problems that are introduced due to inaccuracies in determining the actual depth of the perforations. As stated above, the step of perforating the well typically includes recording the depth and location of the perforations; however, using perforation equipment with both wireline and tubing nevertheless does not always provide accurate depth measurements, due again to the tendency of the tubing or wireline to expand with down hole temperatures or to bend in the borehole.

A need thus exists for a detector that can more reliably detect the presence of anomalies, such as perforations, in the cased borehole. Further, a need exists for a detector that generates a minimal or no magnetic field that would affect the operation of other downhole instrumentation.

Giant magnetoresistive or GMR magnetic field sensors are know for use in high accuracy compasses and geophysical applications such as magnetic field anomaly detection in the earth's crust. GMR sensors are constructed from alternating, ultrathin layers of magnetic and non-magnetic materials. GMR sensors provide high sensitivity to changes in a nearby or surrounding magnetic field. GMR sensors of this type are described in the prior art NVE brochure entitled "NVE—Nonvolatile Electronics, Inc. The GMR Specialists" with errata sheets, and are currently manufactured and marketed by Nonvolatile Electronics, Inc., 11409 Valley View Road, Eden Prairie, Minn. 55344-3617, (612) 829-9217. The GMR sensor uses a "giant magnetoresistive effect" to detect a change in electrical resistance that occurs when stacked layers of ferromagnetic and non-magnetic materials are exposed to a magnetic field.

The present invention overcomes the deficiencies in the prior art.

SUMMARY OF THE INVENTION

The present invention provides an apparatus and methods for reliably detecting, identifying, and locating anomalies in a casing string extending into a wellbore. The apparatus and methods include a detector assembly with a sensor that can sense casing anomalies that vary the magnitude of the magnetic field or that have fringe effects that cause perturbations, or changes, in magnetic fields that are induced in the casing sections by the earth's natural magnetic field.

To detect casing joints, the induced magnetic fields include attractive forces that result from magnetic fringe effects proximate the longitudinal ends of the casing sections. The attractive forces are present at the connective joints of the casing string, thus presenting perturbations in the magnetic fields associated with the casing. The inventive methods and apparatus will detect voids, such as gaps and discontinuities, associated with a casing joint as well as an increased thickness caused by an upset or external collar associated with a casing joint. Thus, the inventive methods and apparatus are capable of detecting flush joints as well as other conventional casing joints.

The apparatus and methods also provide clear and reliable signals indicative of the presence of small anomalies including perforations which are small in size and flush joints where there is no appreciable change in the diameter of the casing at the joint. As a result, the possibility of a well operator failing to recognize such a signal is minimized.

The detector assembly of the present invention generates essentially no magnetic or electromagnetic field. As a result, the presence of the detector does not affect other downhole instrumentation. The detector assembly relies upon the earth's natural magnetic field to polarize and thus induce a magnetic field in the surrounding casing sections. The detector assembly detects perturbations in this naturally-induced magnetic field, such as will result from the fringe effects associated with anomalies, such as gaps, holes, or discontinuities in the casing wall. The detector assembly also easily detects the magnetic signature associated with the presence of a surrounding casing collar.

Further, methods and apparatus of the present invention provide for accurate measurement of lengths and distances, such as the length of casing joints or the distance between such joints.

The present invention also provides a detector assembly with a sensor having a very small physical size and that uses very little power. Further, the detector assembly of the present invention does not need to be moved rapidly through the wellbore in order to reliably detect an anomaly in the casing string. Thus, methods are described for "static" detection of casing anomalies where the detector assembly is moved either very slowly or not at all and that detector can still reliably detect the casing joint.

The detector assembly of the present invention can also locate small anomalies or changes in the thickness of the wall of the casing string. For example, the detector assembly can detect, identify, and locate perforations in the casing having a one-quarter inch diameter. Only one sensor is used in the detector assembly for perforation patterns with perforations on only one side of the casing in a given plane perpendicular to the longitudinal axis of the casing. For perforation patterns with perforations on more than one side per plane, more than one sensor is used in the detector assembly to detect the individual perforations. However, with perforation patterns having perforations on more than one side per plane, one sensor can be used to detect the perforation zone of the casing. The detector assembly also locates the perforations by determining the depth and angular orientation of the perforations for setting one or more packers in the casing string.

Thus, the preferred and alternative embodiments comprise a combination of features and advantages that enable them to overcome various problems of prior art devices. The various characteristics described above, as well as other features, will be readily apparent to those skilled in the art upon reading the following detailed description of the preferred and alternative embodiments, and by referring to the accompanying drawings.

BRIEF DESCRIPTION OF THE DRAWINGS

For a more detailed description of the preferred and alternative embodiments, reference will now be made to the following accompanying drawings:

FIG. 11 is an elevation view of a perforated casing having perforations in a spiral pattern;

FIG. 12 is a cross section view of a perforated casing having perforations which are opposed to each other.

DETAILED DESCRIPTION OF THE PREFERRED AND ALTERNATIVE EMBODIMENTS

The apparatus and methods of the present invention relate generally to detecting, identifying, and locating anomalies in the wall of a string of tubular members by sensing changes or perturbations in natural magnetic fields induced within the string. The present invention is not limited to any particular type of anomalies and in particular is not limited to casing joints and perforations which are described as examples of the application of the apparatus and methods of the present invention. The drawings and the description below disclose in detail specific embodiments of the present invention with the understanding that this disclosure is to be considered an exemplification of the principles of the invention, and is not intended to limit the invention to that illustrated and described in the disclosure. Further, it is to be fully recognized that the different teachings of the embodiments discussed below may be employed separately or in any suitable combination to produce desired results.

Figure 1:
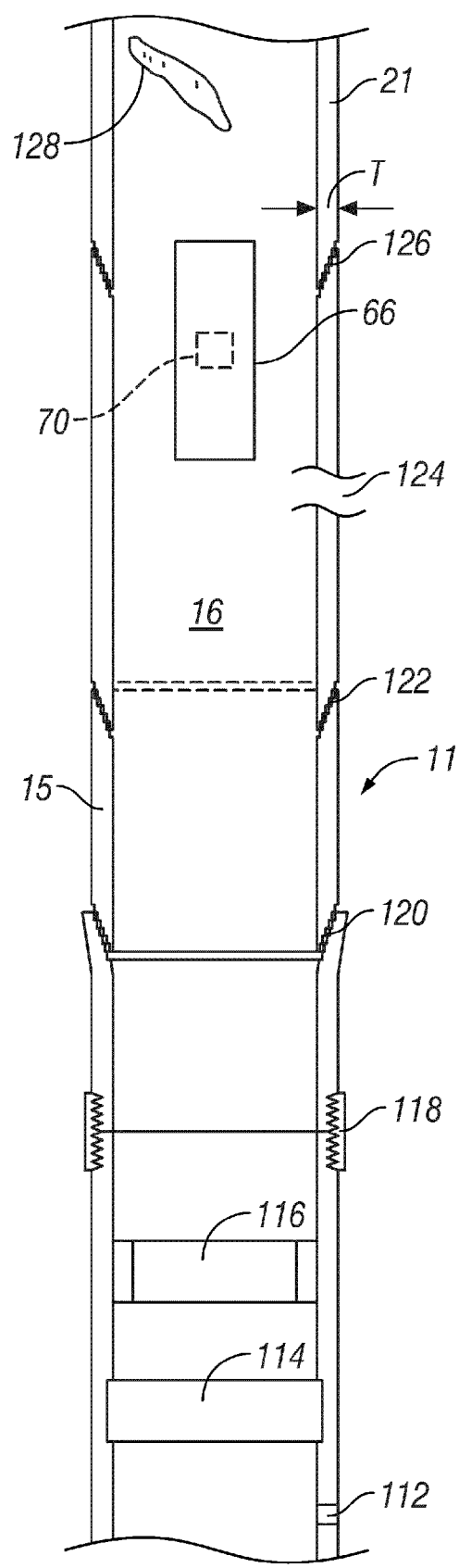
FIG. 1 is a cross-section through the casing string illustrating various examples of anomalies which may be detected, identified and located by the detector assembly of the present invention.

Referring initially to FIG. 1, a detector assembly 66 includes one or more sensors 70 for detecting, identifying, and locating anomalies in the steel or metal casing 14 making up the casing string 11 disposed in the borehole of a well. An anomaly is defined as any variance in the thickness T in the wall 21 forming bore 16 including the absence of thickness, such as a hole through the casing wall. Thickness T is defined as the uniform thickness of the blank portion 15 of the tubular member making up a casing section between the threaded end connections or joints.

FIG. 1 illustrates various examples of anomalies which may be detected, identified, and/or located by detector assembly 66. It should be appreciated that the anomalies shown in FIG. 1 are only illustrative of anomalies in a casing string and should not be considered limiting of the anomalies which may be detected, identified and/or located by detector assembly 66. FIG. 1 illustrates various anomalies including a hole 112 passing through the wall 21 of casing string 11, an internal profile 114 for locating a well tool or tubular member for performing a well operation within the well, a well reference member 116 permanently disposed within a casing section downhole for locating a well tool or tubular member downhole, a casing collar connection joint 118 increasing the thickness T of the casing string 11, a upset casing joint 120 forming an annular gap in the interior of casing string 11, another casing joint 122 forming an external angular gap, damage 124 to the casing, a flush joint 126 having air gaps in the threads, and a scar 128 on the exterior wall of casing string 11. All of the above are examples of anomalies. It should be appreciated that some anomalies relate to variations in the thickness T of wall 21, others include a reduction of the mass at a particular point in the wall 21 of casing string 11 and others include an aperture, hole, or perforation extending completely through the wall 21 of casing string 11. It also can be seen that anomalies may include annular anomalies which extend around the internal or external circumference of wall 21, others include air pockets or gaps interior to wall 21, and other anomalies include a reduction in the interior or exterior mass of the wall 21 due to scarring or other damage to the wall surface.

It should be appreciated that detector assembly 66 may be used to detect an anomaly or may be used to identify an anomaly, or may be used to locate an anomaly. Detector assembly 66 may also be used to measure the dimensions of an anomaly. In locating an anomaly, detector assembly 66 may determine the depth of the anomaly, depth being the distance between the anomaly and the surface measured through the bore of casing string 11, and may determine the angular orientation of the anomaly within the cylindrical wall 21 of casing string 11. In a vertical casing string, the angular orientation will be the azimuth of the anomaly.

The sensor 70 senses an increase or decrease in the mass of the wall 21 at a particular point along casing string 11 as well as senses the absence of mass. Anomalies which include breaks in the interior surface of wall 21 form fringe effects which cause perturbations in the naturally induced magnetic field of the wall 21 of casing string 11. The variation in mass and/or the fringe effects alter the external magnetic field around sensor 70 causing an increase or decrease in the resistance of sensor 70 thereby altering the flow of current through sensor 70. A signal is generated by the change in current flow and the signal is transmitted to the surface to provide a detection, identification, or location of the anomaly in casing string 11.

Referring now to FIGS. 2–5, there is shown an example of using the detector assembly 66 for detecting, identifying and locating a casing joint in the casing string. A borehole section 10 is depicted extending through a formation 12 in the earth. The borehole section 10 includes a string 11 of steel or metal tubular casing 14 forming a cylindrical wall 21 that encloses and defines bore 16 therethrough. Cement 18 surrounds the radial exterior of the casing 14.

Figure 2:
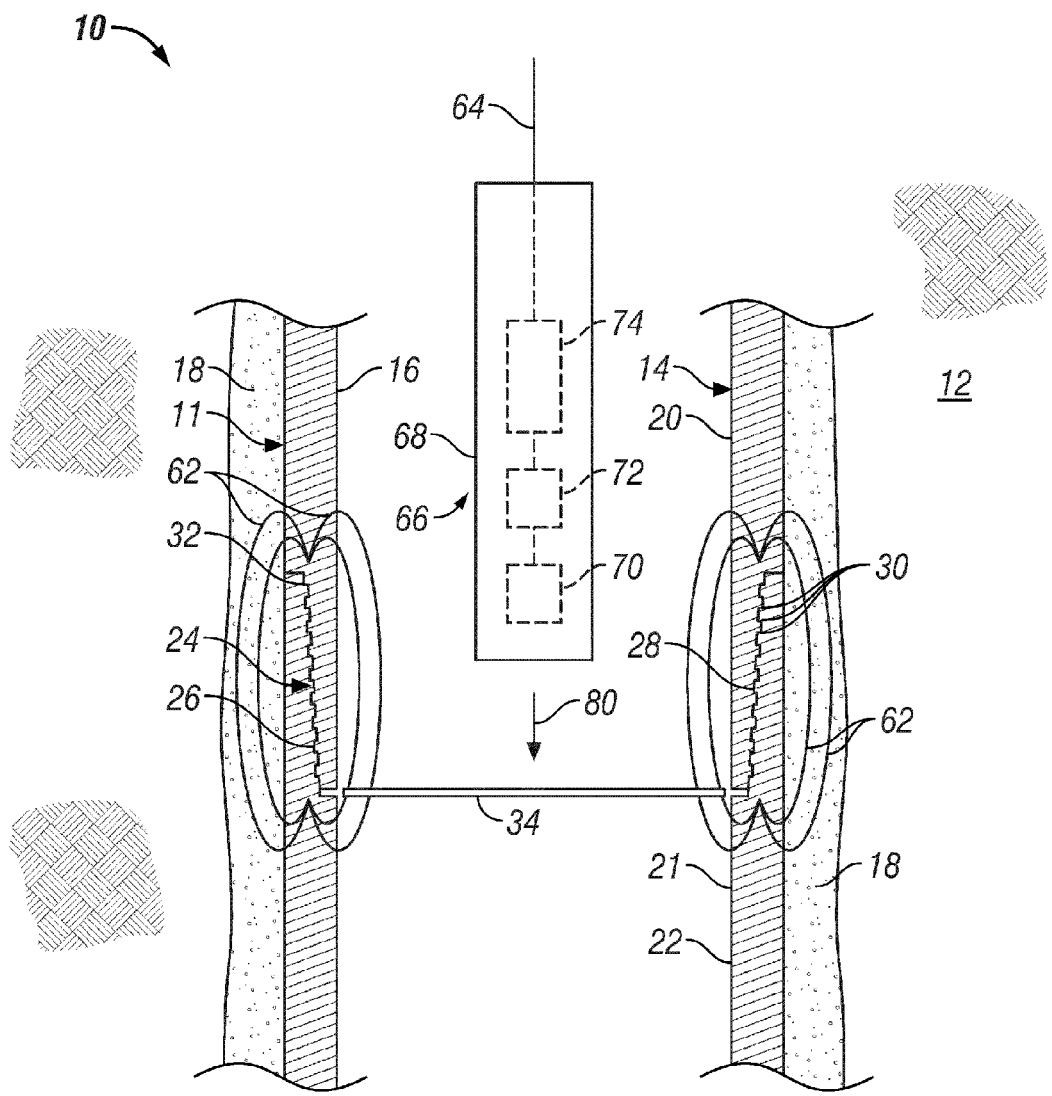
FIGS. 2–4 are cutaway side views of a pair of casing sections joined to one another by a flush joint and containing an exemplary locator for casing joints constructed in accordance with the present invention.
Figure 3:
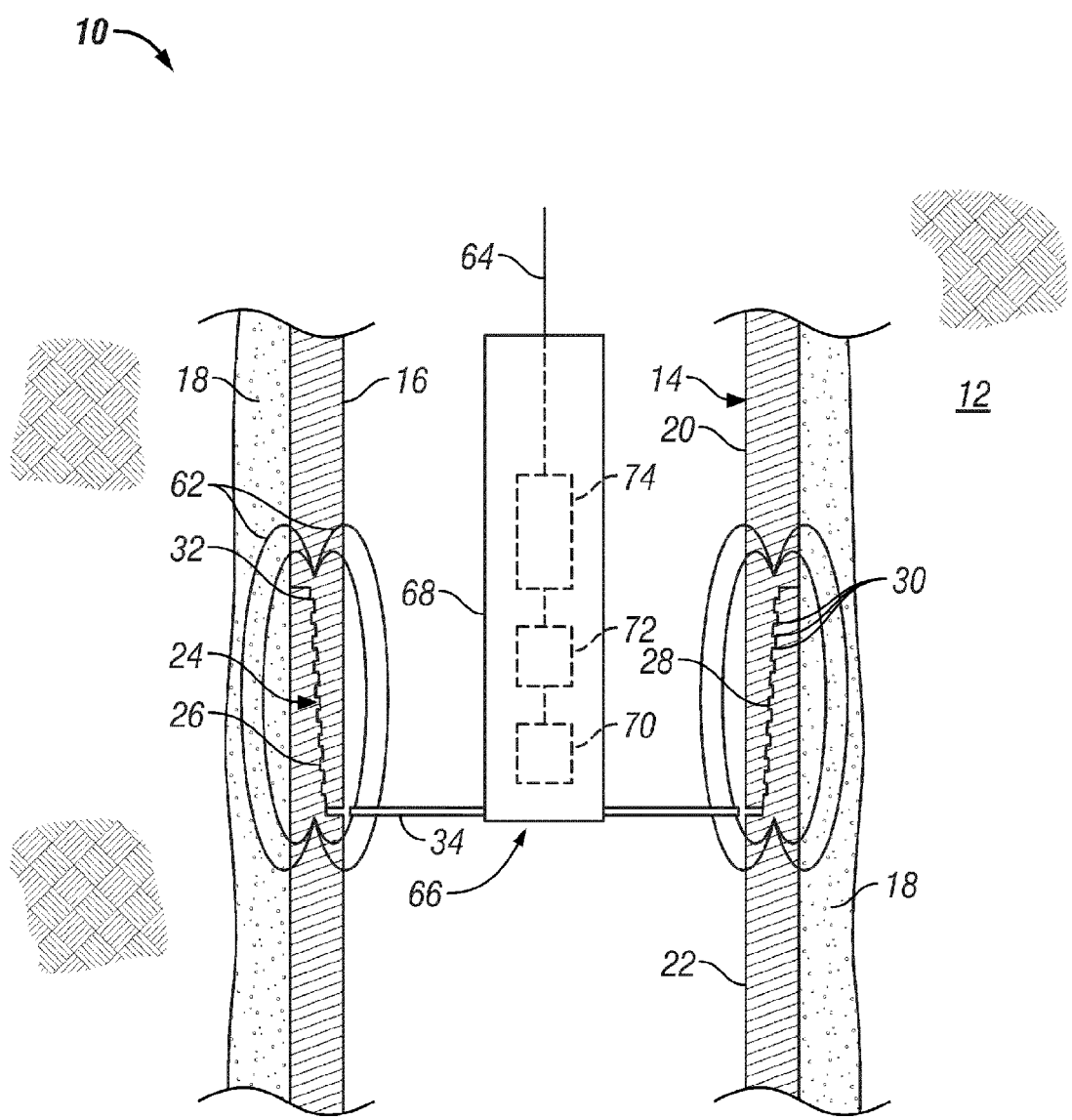
Figure 4:
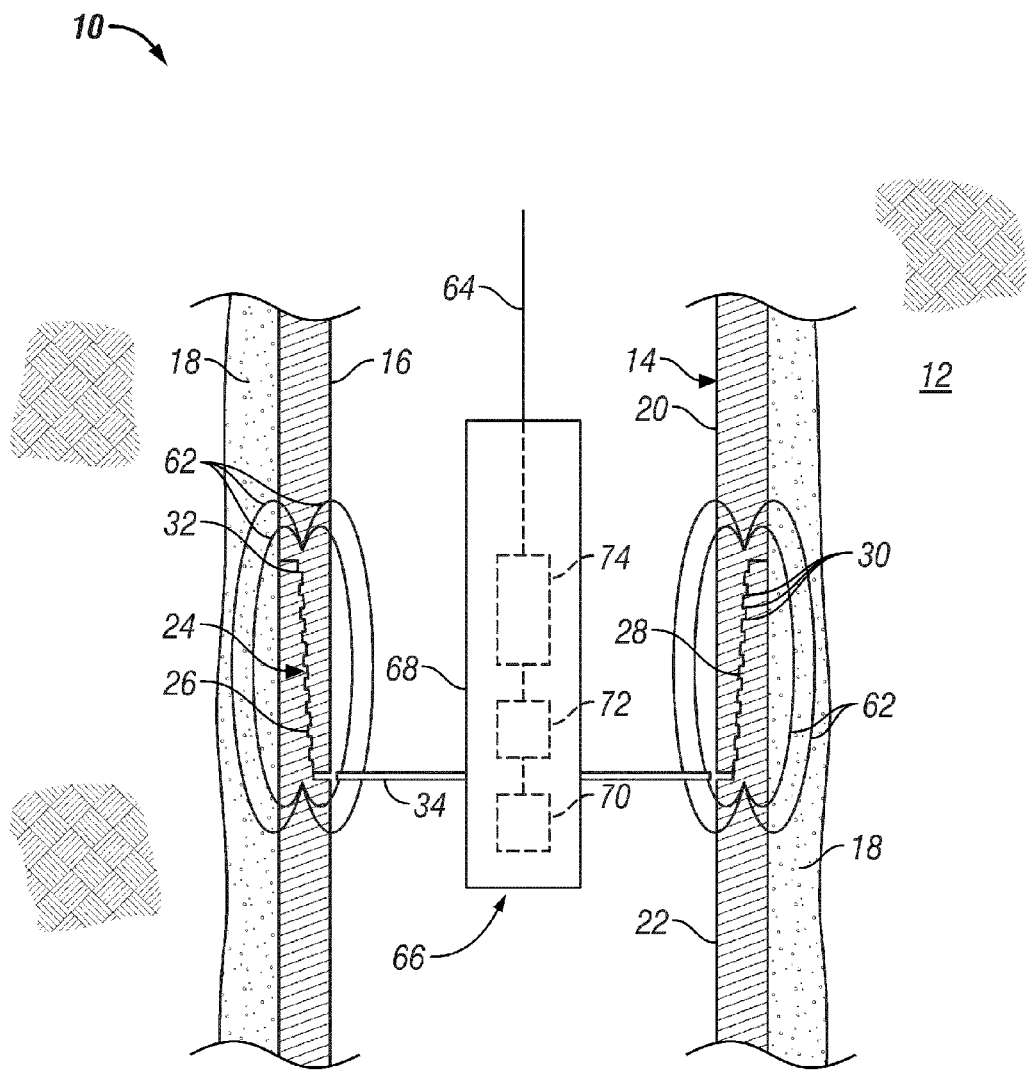

A plurality of elongated tubular casing sections makes up the string of casing 14. Two representative casing sections 20, 22 are shown affixed to one another at a threaded joint 24 that is shown in FIGS. 2–4 and in a closer view in FIG. 5. The joint 24 is made up of a pin-type connector 26 on the upper casing section 20, which is secured within a complimentary box-type connector 28 on the lower casing section 22. The particular joint depicted in FIGS. 2–5 is a flush joint wherein there is little or no change in the thickness T of the casing 14 at the joint. As is apparent, there is no external collar used to join the two casing sections.

Figure 5:
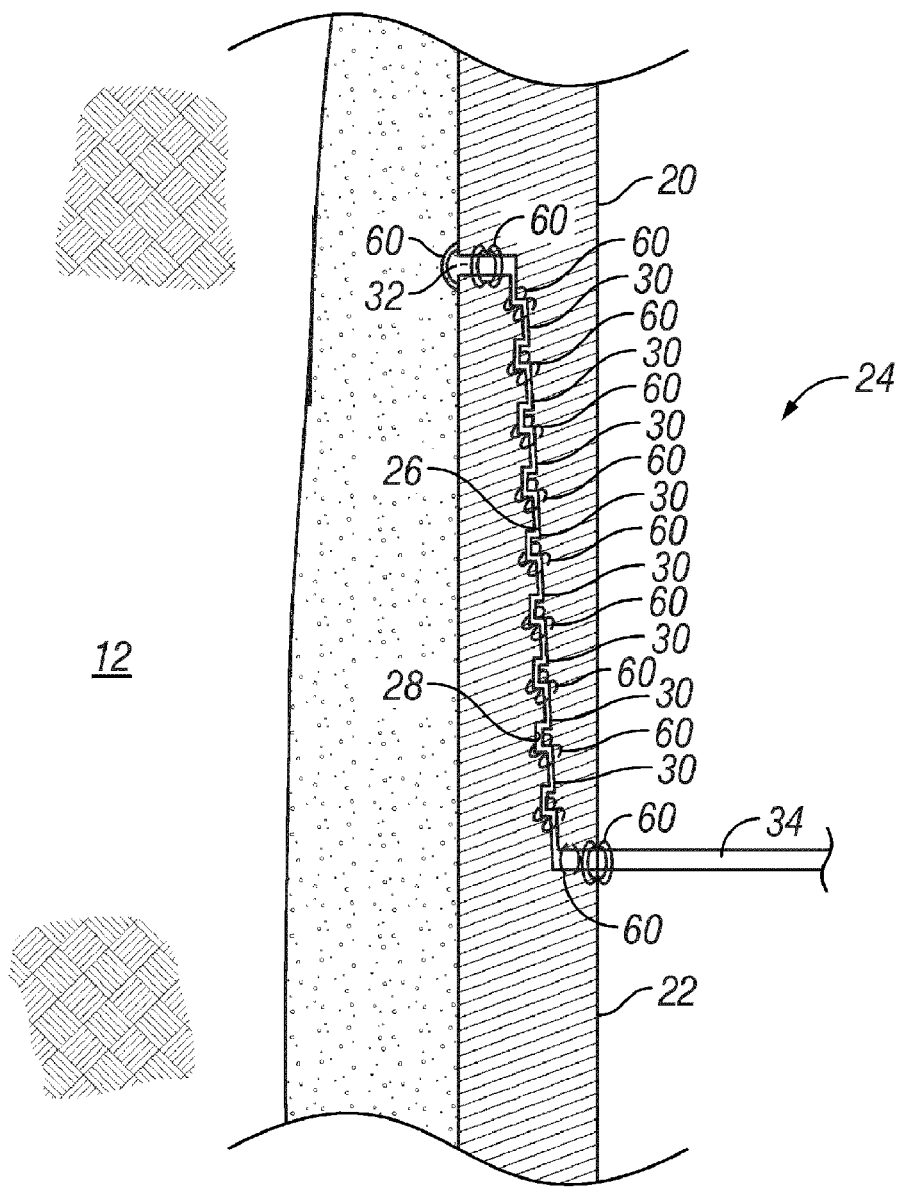
FIG. 5 is an enlarged view of a portion of a flush casing joint.

The threads of the joint 24 include a plurality of air gaps 30, best shown in FIG. 5, that are inherent in any such threaded connection where the generally complimentary threads of the two sections 20, 22 are interleaved. Further, discontinuities in the form of annular gaps 32, 34 are present at either end of the threaded joint 24. Gaps 32, 34 are formed between the terminal end of the casing section 20, 22 and the shoulders 25, 27 at the base of the threads on sections 20, 22, respectively.

Figure 6:
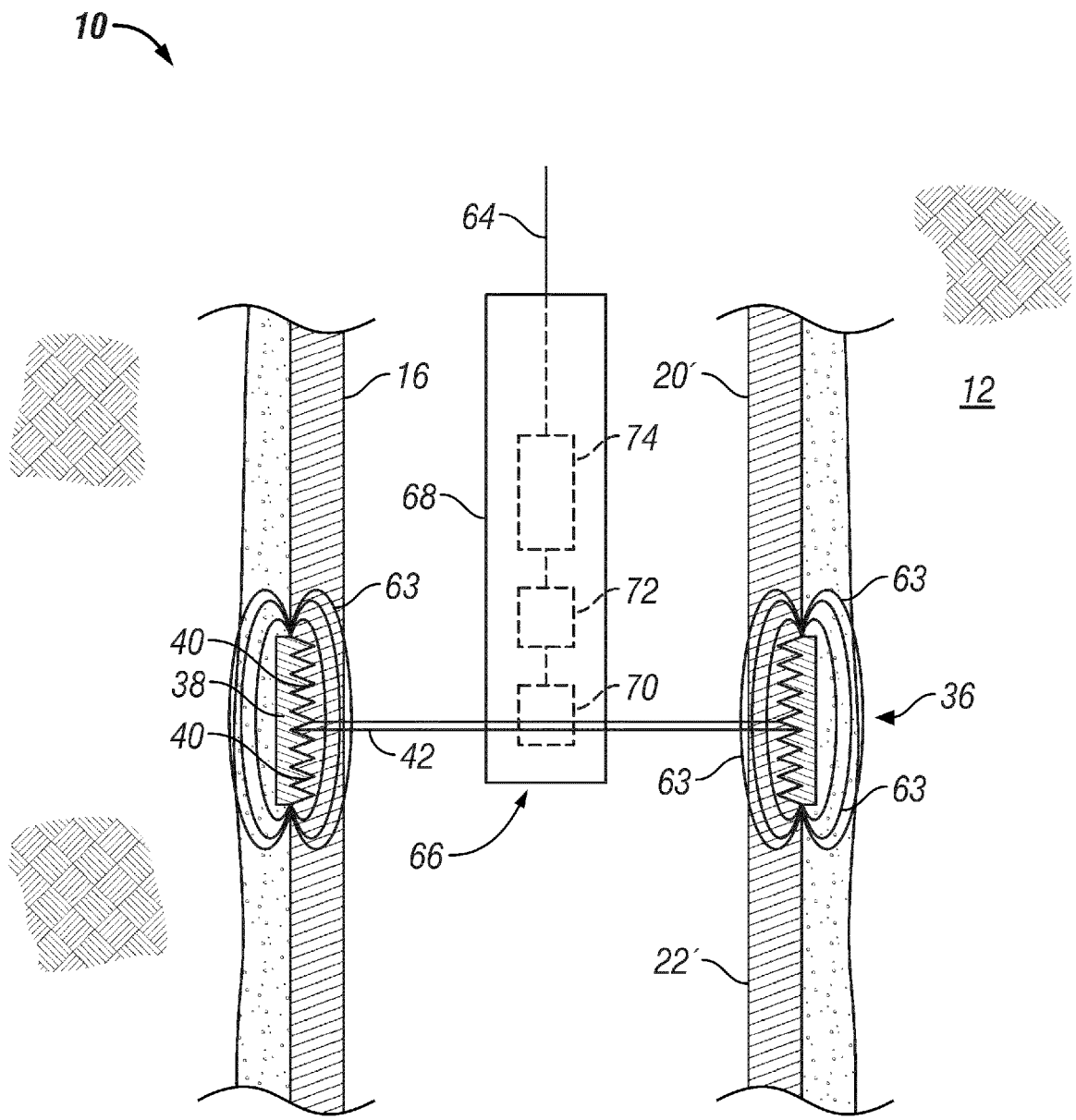
FIG. 6 is a cutaway side view of a pair of casing sections joined by an external collar connection and containing an exemplary locator for casing joints constructed in accordance with the present invention.

FIG. 6 depicts a more conventional casing collar joint 36 in which the pair of casing sections, designated as 20' and 22', are interconnected by a threaded collar 38 that is used to secure a pair of pin-type connectors 40. A discontinuity in the form of annular gap 42 is present between the terminal ends of the two adjacent casing sections 20' and 22'.

Figure 7:
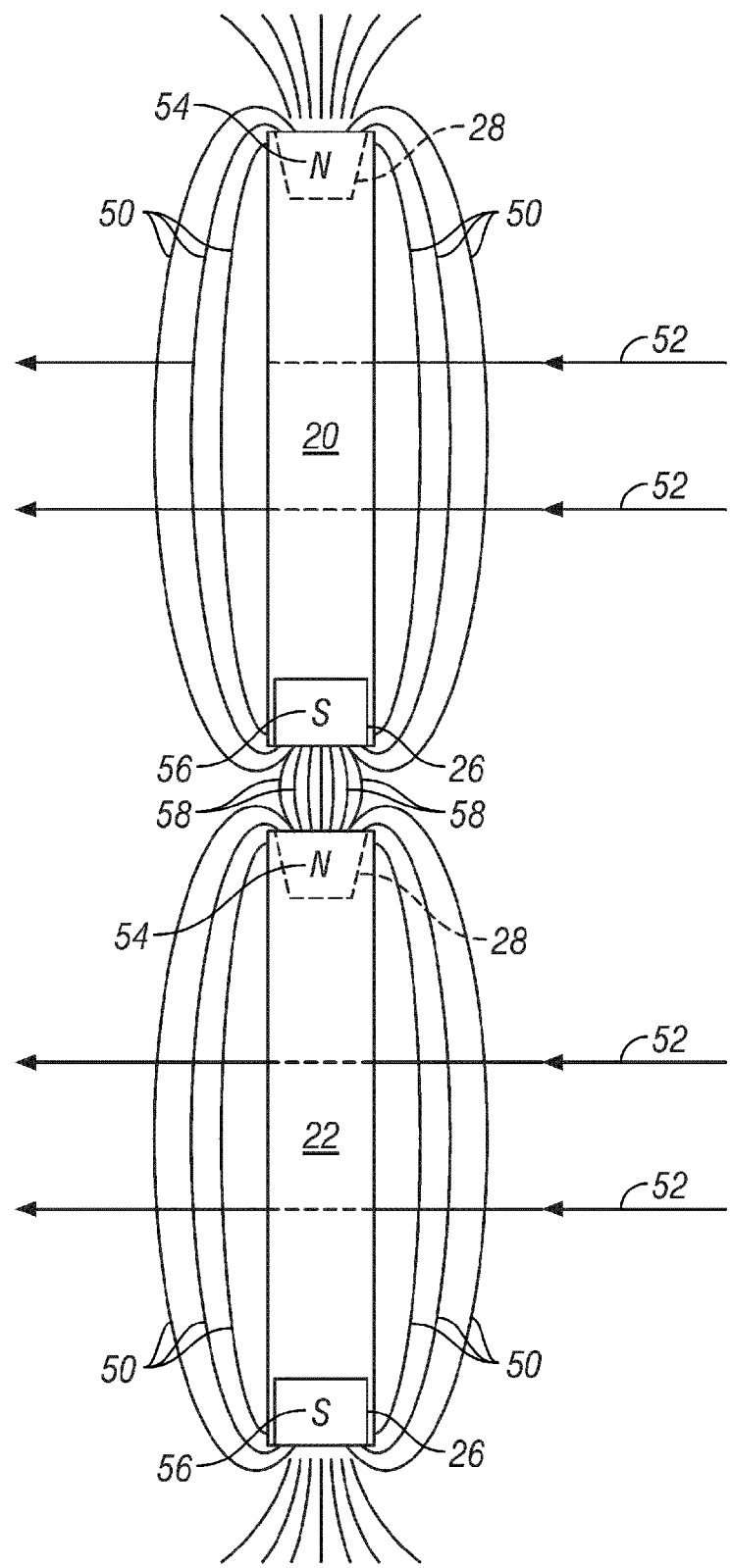
FIG. 7 illustrates the induction of magnetic forces in a pair of casing sections.

The earth's natural magnetic field causes metallic casing sections to act as magnetic dipoles, thus providing their own naturally induced magnetic fields. Referring for the moment to FIG. 7, illustrative magnetic lines of force 50 are depicted around casing sections 20, 22. The magnetic lines of force 50 show a magnetic field that is induced within the casing sections 20, 22 by the earth's natural magnetic field 52, or the magnetic forces travelling from the magnetic north to south poles of the earth. As a practical matter, the induced magnetic field 52 is very weak, but it is capable of being detected by suitably sensitive instrumentation. In essence, the natural field 52 polarizes each section 20, 22 to act as a dipole, providing attractive magnetic forces 50 running from their north poles 54 to their south poles 56. Each casing section 20, 22 is polarized in a common direction so that their north and south poles 54, 56 are commonly oriented. In addition, it should be understood that when the casing sections are interconnected, the entire casing string thus formed will act as a single dipole to some extent as well.

It is well known that the magnetic field is stronger proximate the north and south ends of a dipole. When the casing sections 20, 22 are placed close to one another in an end-to-end relation, as depicted in FIG. 7, there are attractive magnetic end effects, or "fringe effects," 58 that act between the two adjacent casing sections 20, 22. When the two casing sections 20, 22 are joined to one another via a threaded connection 24 (or 36), the fringe effects 58 continue to provide lines of attractive magnetic force between portions of the interconnected casing sections at and around the connection point. These lines of attractive force generally correspond to the presence of small gaps or separations, such as at 30, between the two sections. By way of example, FIG. 5 is a close up view of a portion of the threaded flush joint connection 24 showing illustrative lines for these attractive forces 60 located at the gaps 26 and the discontinuities 28 and 29 for the connection. The aggregate of these small attractive forces 60 leads to an increased fringe effect magnetic signature 62 that is depicted by magnetic force lines in FIGS. 2–4.

An increase localized magnetic signature 63 is also shown to be associated with the collar joint 36 in FIG. 6. This signature 63 results from the increase mass of metal provided by the external collar 38 as well as the attractive magnetic effects associated with the discontinuity 42 in the wall of the casing string.

FIGS. 2–4 and 6 also show suspended within the bore 16 of the string of casing 14, a wireline 64 that is disposed into the wellbore 16 from the surface (not shown). The wireline 64 is adapted to transmit power and data in the form of a modulated electrical signal. It is preferred that the wireline 64 include power and ground wires, data transmission lines, and command/response transmission lines. The wireline 64 also supports detector assembly 66 that includes a pressure barrel 68 constructed of a non-magnetic material such as beryllium copper. The pressure barrel 68 is constructed to be resistant to fluids and capable of withstanding downhole pressures without collapsing. It should be appreciated that detector assembly 66 may be suspended on tubing rather than a wireline.

The sensor 70 in detector assembly 66 may be a "giant magnetoresistive," or GMR magnetic field sensor that is housed within the pressure barrel 68. GMR sensors are constructed from alternating, ultrathin layers of magnetic and non-magnetic materials. GMR sensors provide high sensitivity to changes in a nearby or surrounding magnetic field. GMR sensors of this type are currently manufactured and marketed by Nonvolatile Electronics, Inc., 11409 Valley View Road, Eden Prairie, Minn. 55344-3617, (612) 829-9217. The GMR sensor is adapted to detect a change in a surrounding magnetic field and, in response thereto, generate a signal indicative of the change. The sensitivity of the GMR sensor permits detection of small anomalies in the surrounding magnetic structure, such as the gaps 30 and the discontinuities 32, 34 of the casing joint 24. As a result, joints between a pair of interconnected casing sections can be detected by the detector assembly 66. It is noted that a GMR sensor itself generates essentially no magnetic signature and, therefore, will not affect the operation of other downhole equipment that detect or rely upon magnetic readings.

Figure 8A:
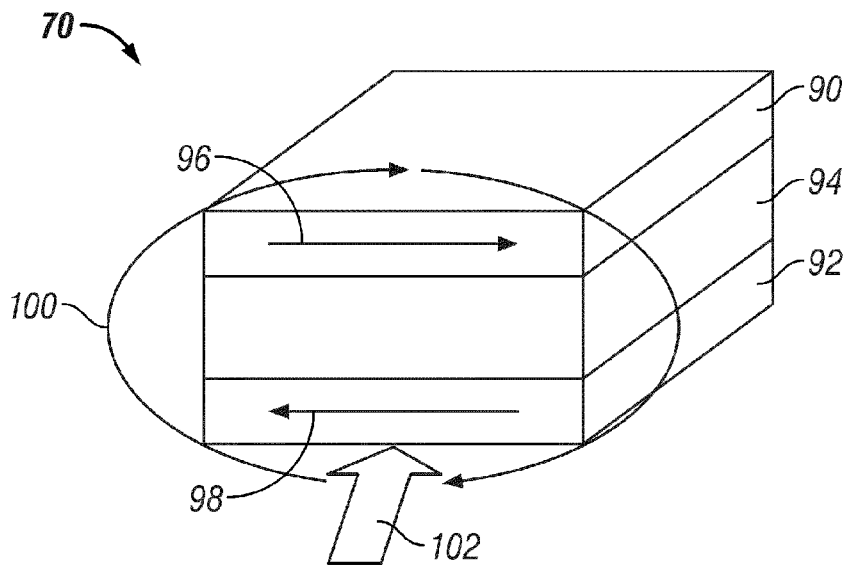
FIG. 8A is a schematic of a sensor without an external magnetic field and FIG. 8B is a schematic of a sensor with an external magnetic field.

Referring now to FIGS. 8A and B, there is shown a schematic of a "giant magnetoresistive," or GMR magnetic field sensor 70 described in the prior art NVE brochure entitled "NVE—Nonvolatile Electronics, Inc. The GMR Specialists" with errata sheets, all hereby incorporated herein by reference. The "giant magnetoresistive effect" is a change in electrical resistance that occurs when stacked layers of ferromagnetic and non-magnetic materials are exposed to a magnetic field. High sensitivity low field GMR materials are to be used in high accuracy compasses and geophysical applications such as magnetic field anomaly detection in the earth's crust.

Figure 8B:
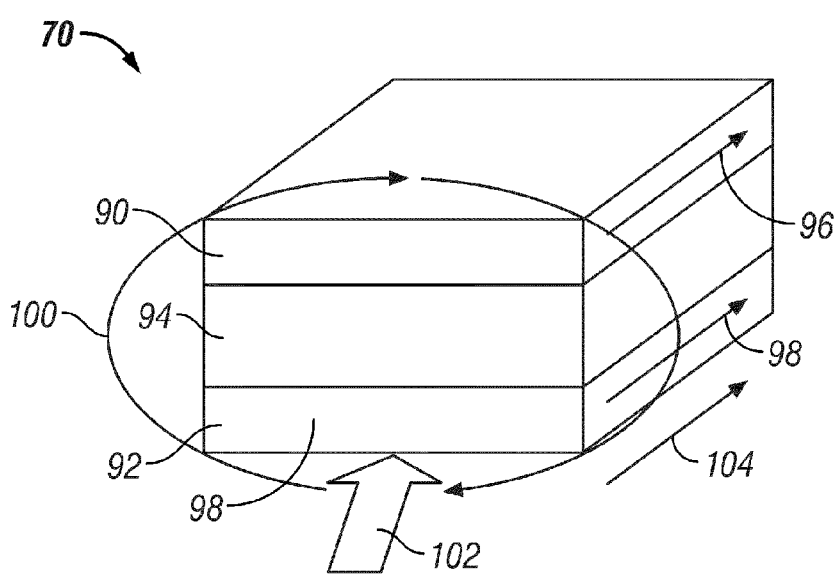

FIG. 8A illustrates sensor 70 with no external magnetic field and FIG. 8B illustrates sensor 70 with an external magnetic field. Sensor 70 includes alternating layers of magnetic and nonmagnetic materials. In a typical sensor 70, there are two layers of magnetic material 90, 92, such as an alloy, which are separated by an interlayer of a conductive, nonmagnetic material 94. A magnetic field 100 applied to sensor 70 induces a current 102 to flow through materials 90, 92, 94 which provide a resistance. The resistance to current 102 is high. Referring to FIG. 8A and as shown by arrows 96, 98, the magnetic moments in magnetic materials 90, 92 face opposite directions due to magnetic field 100. Referring to FIG. 8B, applying an external magnetic field 104 causes the magnetic moments 96, 98 to line up in the direction of the current 102 from magnetic field 100. Electrical resistance drops dramatically. As the external magnetic field 104 varies, the current varies.

The sensor 70 is very small having typical dimensions of 0.154 inches by 0.193 inches by 0.054 inches. Thus, sensor 70 is sufficiently sensitive to detect perturbations of a similar size, i.e., substantially less than an inch. The advantages of the GMR sensor include reduced size, high signal level, high sensitivity, high temperature stability, and low power consumption.

The detector assembly 66 also includes a signal processor 72 that is operably interconnected with the sensor 70. The signal processor 72 receives the signal provided by the sensor 70, amplifies the signal, and shapes it in order to provide a processed signal more recognizable. At the surface, in the preferred embodiment described here, the processed signal features a readily recognizable square wave, the high state portion of which corresponds to the presence of a joint. The signal processor 72 includes an amplifier and an analog-to-digital converter (neither shown), which are well-known components. The amplifier enhances the signal while the converter is used to convert the analog readings obtained by the sensor 70 into a more readily recognizable digital signal. If desired, the signal processor 72 may incorporate one or more noise filters of a type known in the art in order to remove noise from the signal generated by the sensor 70. Other signal processing techniques used to enhance the quality of such signals may be applied.

The detector assembly 66 further includes a data transmitter 74 that is operably interconnected with the signal processor 72. The data transmitter 74 receives the amplified and processed signal created by the signal processor 72 and transmits it to a distant receiver, typically located at the surface of the wellbore that includes borehole section 10. The distant receiver might comprise an oscilloscope, computer, or storage medium for the signals.

In operation, the sensor 70 senses the perturbation provided by the increased or changed magnetic fields associated with anomalies in the wall of the casing string, such as the connections or joints between casing sections 20, 22 or 20', 22'. In the case of the collar connection 36 shown in FIG. 6, the sensor 70 senses the increased magnetic field in the surrounding casing resulting from the presence of the external collar 38 as well as that provided by the discontinuity 42.

Figure 9:
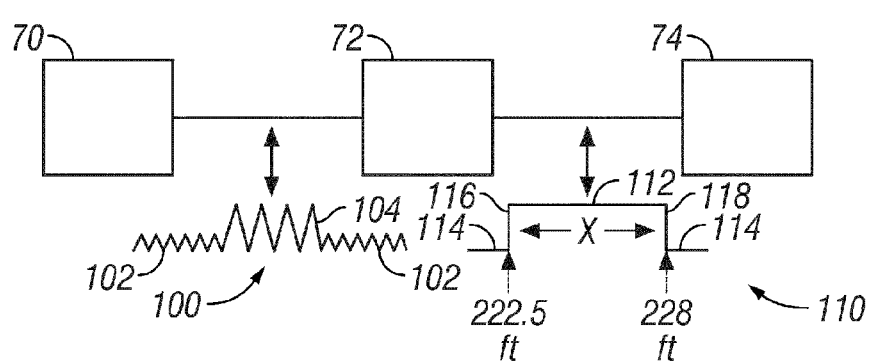
FIG. 9 is a schematic diagram illustrating exemplary signals received and generated by the signal processor.

FIG. 9 illustrates the processing of the signals by the signal processor 72. The sensor 70 sends an analog signal 100 to the processor 72. As shown, the analog signal 100 is made up of a number of peaks and valleys that correspond to changes in the magnetic field sensed by the sensor 70. The analog signal 100 includes a reduced baseline signal portion 102 that corresponds to detection by the sensor 70 of continuous casing walls. The signal 100 also includes an enhanced signal portion 104 that corresponds to the detection by the sensor 70 of anomalies, such as discontinuities, holes, or gaps in the surrounding casing walls. The enhanced signal portion 104 is significantly different from the baseline signal portion 102 due to changes in the borehole magnetic flux as a result of the discontinuities 32, 34 and gaps 30 present in the casing 14. As noted, the signal processor 72 contains an amplifier and analog-to-digital converter, both of which are well-known components. The signal processor 38, therefore, produces a processed digital signal 110 based upon the analog signal 100 it receives. The processed signal 110 is preferably a square wave that is made up of "high" and "low" states, each of which are indicative of a different condition. This type of signal is preferred because it provides a more definite indication of condition than an analog signal such as signal 100. The high state portion 112 of the signal 100 is indicative of the presence of discontinuities and/or gaps in the surrounding casing wall and is produced when the sensor 70 is located adjacent a casing joint, such as joint 24. Conversely, a low state portion 114 results when there is an absence of such discontinuities and gaps. The processed signal 110 is received by and then transmitted to the surface via the data transmitter 74 on a periodic basis, such as every 50 milliseconds.

As explained, the high state portion 112 of the square wave of the processed signal 110 corresponds to the presence of anomalies, such as discontinuities, gaps, and/or casing mass change in the surrounding casing wall, while the low state portion 114 of the signal 110 indicates the absence of anomalies, such as discontinuities, gaps, and wall mass change, that would affect the surrounding magnetic field. As a result, the length ("x" in FIG. 5) of the high state portion 112 corresponds to the length of the joint 24 as measured from the upper discontinuity 32 to the lower discontinuity 34. The detector assembly 66 permits the determination of the length of the joint 24 from the length "x" of the high state portion 112 of the signal 110. This capability provides well operators with greater information regarding the exact location and sizes of joints within a cased wellbore and is, therefore, quite valuable. More specifically, the detector assembly 66 is typically moved at a relatively constant rate, or velocity, through the wellbore 10. This rate is known and controlled at the surface. When this is the case, the detector assembly 66 is initially positioned at a known depth or location in the cased wellbore. If the initial position for the detector assembly 66 is at the surface of the well, the initial position will be at zero (0) feet. As the detector assembly 66 is lowered though the wellbore, the signal 110 is normally transmitted to the surface, or updated, in a periodic fashion over time, i.e., every 50 milliseconds. Because the velocity of movement (v) of the detector assembly 66 through the cased wellbore is known and the time (t) of the signals is known, the location of the detector assembly 66 within the well can be determined. Further, the location of the detector assembly 66 can be referenced to the presence of a joint between casing sections so that the location of these joints is easily tracked and determined. Additionally, the signal length ("x"), discussed earlier, can be easily correlated to the length of a certain joint so that the actual length of the joint as well as the exact depth of portions of the joint can be determined.

The example is further illustrated in FIG. 9 where the analog signal 100 changes from its baseline signal 102 to the enhanced signal 104 upon encountering the leading portion of a joint, such as the upper discontinuity 32 of joint 24. The signal processor 72 converts the analog signal to the processed signal 110 and, when the leading portion of the joint 24 is detected by the sensor 70, the processed signal 110 changes from a low state signal 114 to a high state signal 112 at point 116. At the surface, point 116 is correlated with a depth marker (e.g., 222.5 ft.), as calculated by the velocity vs. time relationship described earlier. Such correlation can be easily accomplished using known software to make the appropriate calculations. As the sensor 70 is moved downwardly and past the lower portion of the joint 24, the processed signal 110 changes from a high state signal 112 to a low state signal 114 at point 118. Point 118 is also correlated with a depth marker (e.g., 228 ft.). The difference between points 116 and 118 yields 5.5 ft., the length of the joint 24.

Operation of the detector assembly 66 in an exemplary wellbore is illustrated by the sequence of FIGS. 2–4 that show the detector assembly 66 being lowered through the cased borehole section 10. In FIG. 2, the detector assembly 66 is located within the cased borehole section 10 and moved in the direction of arrow 80 until the sensor 70 is substantially adjacent the discontinuity 32 at the upper end of the joint 24. At this point, the discontinuity 32 is detected by the sensor 70 and a processed signal 110 is moved to a high state 112 from a low state 114.

In FIG. 3, the sensor 70 is located proximate the gaps 30 of the joint 24. As a result, the processed signal 110 will be maintained in the high state 112 due to the alteration in the surrounding magnetic field caused by gaps 30. In FIG. 4, the detector assembly 66 has moved downwardly to the point where the sensor 70 is disposed below the lower discontinuity 34 and is adjacent the wall of the lower casing section 22. Due to the absence of gaps 30 or discontinuities 32, 34, the processed signal 110 will return to the low state 114.

It should be appreciated that the detector assembly 66 of the present invention may be used to detect any anomaly in the wall of the casing string. For example, detector assembly 66 is useful in detecting breaks or ruptures in the wall of the casing 14. Such breaks and ruptures result in a change, or perturbation, in the induced magnetic fields in the wall of the casing string. As a result, the detector assembly 66 may be used to find damage in a wellbore casing. The methods of detecting such damage are substantially the same as those described above with respect to detecting casing joints.

Figure 10:
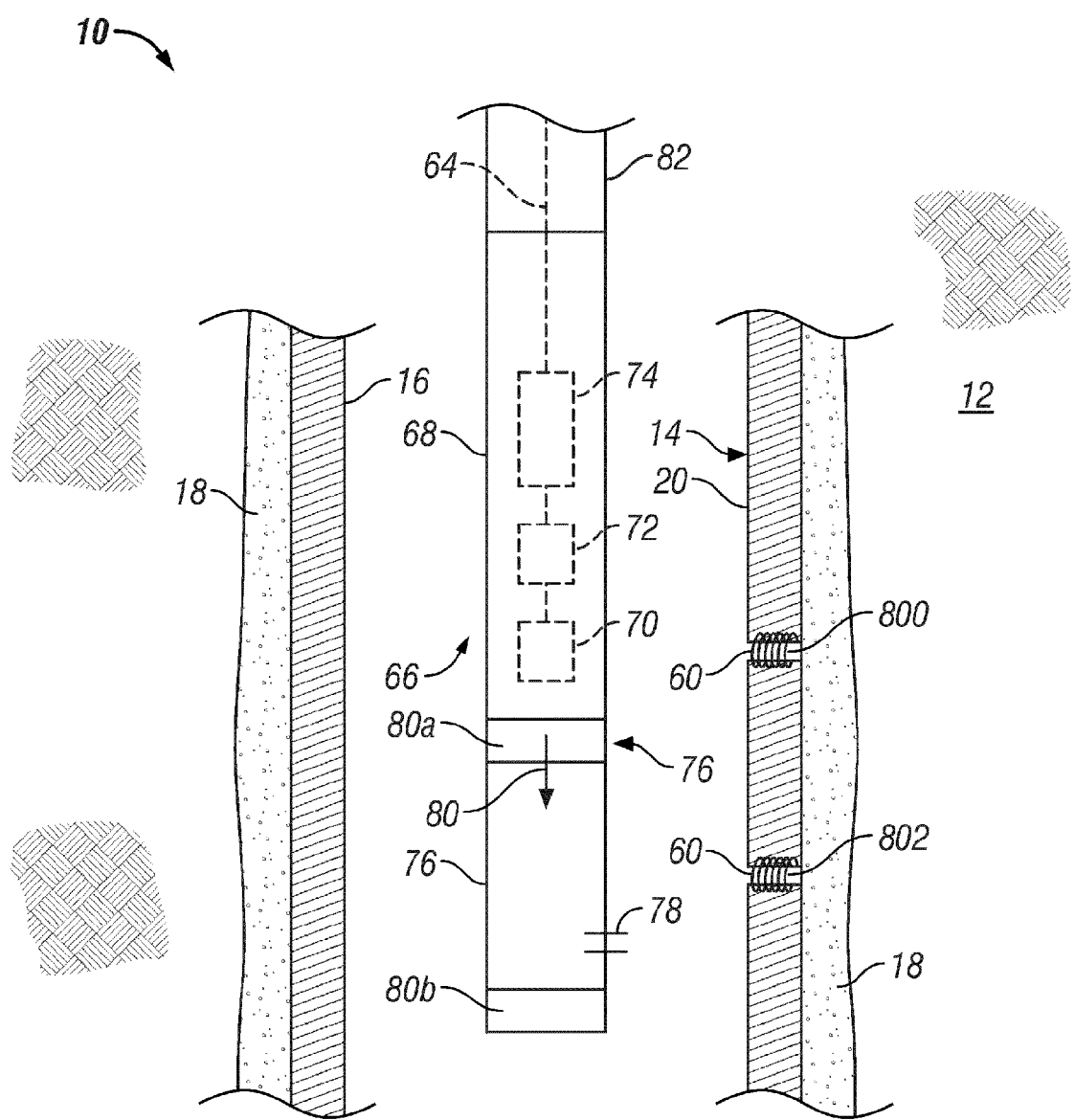
FIG. 10 is a cutaway side view of a casing section with perforations containing an exemplary locator constructed in accordance with the present invention.

Referring now to FIGS. 10–12, there is shown another application of the detector assembly 66 to locate perforations in the casing. The detector assembly 66 is the same as that discussed above. Instead of locating casing joints or casing collars, however, the detector assembly 66 operates in the same manner to detect perforations 800, 802 in the wall of the casing 20. Perforations 800, 802 are small, generally less than one inch in diameter and typically having a diameter of 0.25 inches. Thus, perforations 800, 802 have the same magnetic force qualities as gaps, such as air gaps 30 shown in FIG. 4. Due to the natural magnetic field of the casing 14, the perforations produce fringe effects 58 due to the lines of attractive magnetic forces 60 across the sides of the perforations 800, 802. The attractive magnetic forces 60 produce an increased magnetic signature 63 just as with the casing joints and casing collars discussed above. With a detector assembly 66 having a resolution high enough to detect the increased magnetic signatures of the perforations 800, 802, the exact location of the perforations can be determined. The detection of perforations is sensitive to the location of the perforations 800, 802 and the axial location of the detector assembly 66 in the casing 20.

For perforation patterns with perforations 800, 802 on one side of the casing 20 in a given plane perpendicular to the longitudinal axis of the casing 20 as shown in FIG. 10, only one sensor 70 is needed. For perforation patterns with perforations 800, 802 having a spiral pattern with spiraling rows 804 as shown in FIG. 11, only one sensor may be needed since the perforations are staggered. For perforation patterns with opposing perforations 800, 802 on more than one side of the casing 20 per plane as shown in FIG. 12, more than one sensor 70, such as sensors 70a, 70b, is needed to detect individual opposed perforations. However, with perforation patterns with perforations 800, 802 on more than one side per plane, one sensor 70 may still be used to detect the perforation zone of the casing 20 because it is not necessary to detect the individual perforations 800, 802.

In operation, the detector assembly 66 may be included as part of a bottom hole assembly (BHA) 76 on a workstring 82 when the BHA 76 includes nozzles or ports 78 and one or more packers 80a, 80b. The detector assembly 66 typically has a resolution of approximately 0.1 inch so that it can detect the increased magnetic signature caused by the fringe effects of an anomaly of 0.1 inch or more such as a perforation of approximately 0.25 inch diameter. The BHA 76 is lowered into the casing bore 16 to a depth such that ports 78 are below the region of perforations 800, 802 in casing 20. The BHA 76 is then raised until the detector assembly 66 senses the increased magnetic signature associated with the perforations 800, 802. When the detector assembly 66 locates perforated region in the casing 20, the BHA 76 is raised a known distance such that the ports are substantially aligned with one or more perforations 800, 802. Likewise, the BHA 76 is also raised until the packers 80a, 80b straddle the perforated zone in a blank section of casing (a section free of perforations and casing joints). Once the position is confirmed, the packers are set and the well operation commences. The well operation may include any well stimulation or treatment including fracing, acid treatment, or other operation to enhance production.

Figure 13:
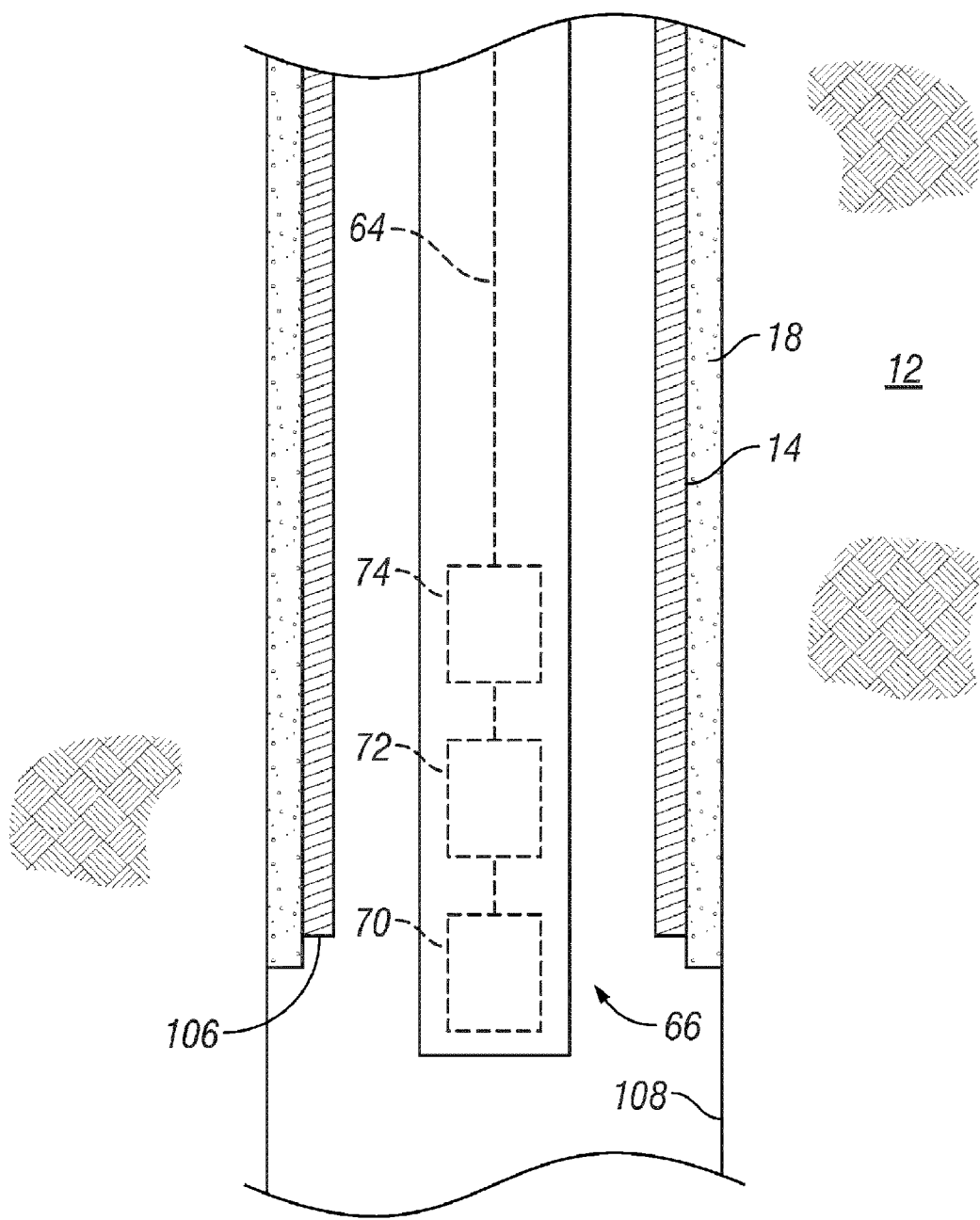
FIG. 13 is a cross-sectional elevation view of the lower end of a cased borehole with an earthen borehole extending below the terminal end of the casing.

Referring now to FIG. 13, there is shown another preferred application of the detector assembly 66 of the present invention. The detector assembly 66 is substantially the same as that previously described. In the preferred method illustrated in FIG. 13, the detector assembly 66 is lowered through a cased borehole with casing 14. The casing 14 is cemented by cement 18 into the borehole extending through formation 12. The casing 14 includes a lower terminal end 106 with the earthen borehole 108 extending below the terminal end 106 of casing 14. During well operations, it may be necessary to locate the lower terminal end 106 of casing 14 so that well operations may be conducted in that portion of borehole 108 extending below casing 14. One such well operation includes drilling a borehole below casing 14 that has a diameter equal to or greater than the outer diameter of casing 14 for disposing additional casing of a similar diameter below casing 14. The detector assembly 66 with sensor 70 passes through borehole 108 to sense the change in the natural magnetic field between casing 14 and the earthen borehole wall of borehole 108 extending below terminal end 106. Not only will there be a reduced magnetic field below terminal end 106, but fringe effects at the terminal end 106 produce perturbations in the magnetic field that sensor 70 detects. The magnetic signature produced by lower terminal end 106 permits the accurate location of terminal end 106 and, in particular, the upper end of the earthen borehole 108 extending below casing 14 for conducting of well operations.

While preferred and alternative embodiments have been shown and described, modifications can be made by one skilled in the art without departing from the spirit or teaching of this invention. The embodiments as described are exemplary only and are not limiting. Many variations and modifications of the system and apparatus are possible and are within the scope of the invention. Accordingly, the scope of protection is not limited to the embodiments described, but is only limited by the claims that follow, the scope of which shall include all equivalents of the subject matter of the claims.

What is claimed is:

1. A method of locating an anomaly in a tubular member in a well, the tubular member having a naturally induced magnetic field, comprising:
    passing a sensor through the tubular member;
    sensing an anomaly in the tubular member causing a fringe effect associated with the naturally induced magnetic field of the tubular member;
    producing a signal from the sensor indicative of the fringe effect associated with the anomaly.

2. The method of claim 1 wherein the anomaly is a perforation in the tubular member.

3. The method of claim 2 wherein the anomaly is a void associated with the perforation.

* * * * *